US008399190B2

(12) United States Patent  
Belgrader et al.

(10) Patent No.: US 8,399,190 B2
(45) Date of Patent: Mar. 19, 2013

(54) MAGNETIC LYSIS METHOD AND DEVICE

(75) Inventors: Philip Belgrader, Severna Park, MD (US); Benjamin Hindson, Livermore, CA (US)

(73) Assignees: Akonni Biosystems, Frederick, MD (US); Quantilife, Inc., Pleasanton, CA (US)

(*) Notice: Subject to any disclaimer, the term of this patent is extended or adjusted under 35 U.S.C. 154(b) by 162 days.

(21) Appl. No.: 12/886,144

(22) Filed: Sep. 20, 2010

(65) Prior Publication Data

US 2011/0070589 A1 Mar. 24, 2011
US 2012/0003654 A2 Jan. 5, 2012

Related U.S. Application Data

(60) Provisional application No. 61/272,396, filed on Sep. 21, 2009.

(51) Int. Cl.
*C12Q 1/68* (2006.01)
*G01N 33/53* (2006.01)
*G01N 33/567* (2006.01)
*C12P 19/34* (2006.01)
*C07H 21/02* (2006.01)

(52) U.S. Cl. ......... 435/6.1; 435/6.11; 435/7.1; 435/7.2; 435/7.21; 435/91.1; 536/23.1

(58) Field of Classification Search .................. 435/6.1, 435/6.11, 6.12, 7.1, 7.2, 7.32, 91.1, 91.2, 435/91.51, 7.21; 436/94, 501; 536/23.1, 536/24.3, 24.33, 25.3
See application file for complete search history.

(56) References Cited

U.S. PATENT DOCUMENTS 5,536,475 A 7/1996 Moubayed et al.
2003/0203491 A1 10/2003 Andrevski et al.
2004/0082779 A1 4/2004 Vos et al.
2008/0063628 A1 3/2008 Davis et al.
2008/0102479 A1 5/2008 Merza

FOREIGN PATENT DOCUMENTS

EP 1234832 A2 8/2002

OTHER PUBLICATIONS

"Stir bar" and "Magnetic stirrer" from Wikipedia, the free encyclopedia. Printed on Sep. 26, 2012.*
Honaker et al., Unique Roles of DosT and DosS in DosR Regulon Induction and *Mycobacterium tuberculosis* Dormancy. Infection and Immunity, 77, 3258-3263, Aug. 2009.*
International Search Report issued in PCT/US2010/002569, dated Jun. 10, 2011.
Written Opinion of the International Search Authority issued in PCT/US2010/002569, Dated Jun. 10, 2011.
Lui, et al., "Nucleic Acid-based Detection of Bacterial Pathogens Using Integrated Microfluidic Platform Systems", Sensors, 2009, pp. 3713-3744, vol. 9.
Smolen, et al., "L-Selectin Signaling of Neutrophil Adhesion and Degranulation Involves p38 Mitogen-activated Protein Kinase", The Journal of Biological Chemistry, May 2000, pp. 15876-15884, vol. 275, No. 21. Trotman, et al., "Calcium Alginate Bead Immobilization of Cells Containing Tyrosine Ammonia Lyase Activity for Use in the Production of p-Hydroxycinnamic Acid", Biotechnol. Prog., 2007, pp. 638-644, vol. 23.
Dittrich, et al., "Micro Total Analysis Systems. Latest Advancements and Trends", Anal. Chem. 2006, pp. 3887-3908, vol. 78.

* cited by examiner

*Primary Examiner* — Frank W Lu
(74) *Attorney, Agent, or Firm* — Michael Ye; Andrews Kurth LLP

(57) ABSTRACT

A method for lysing cells is disclosed. The method includes stirring cells with a magnetic stir element in the presence of a plurality of cell lysis beads at a speed sufficient to lyse the cells. Also disclosed is a device for lysing cells. The device includes a container having a magnetic stir element and a plurality of cell lysis beads disposed therein. The container is dimensioned to allow rotation of the magnetic stir element inside the container.

23 Claims, 10 Drawing Sheets

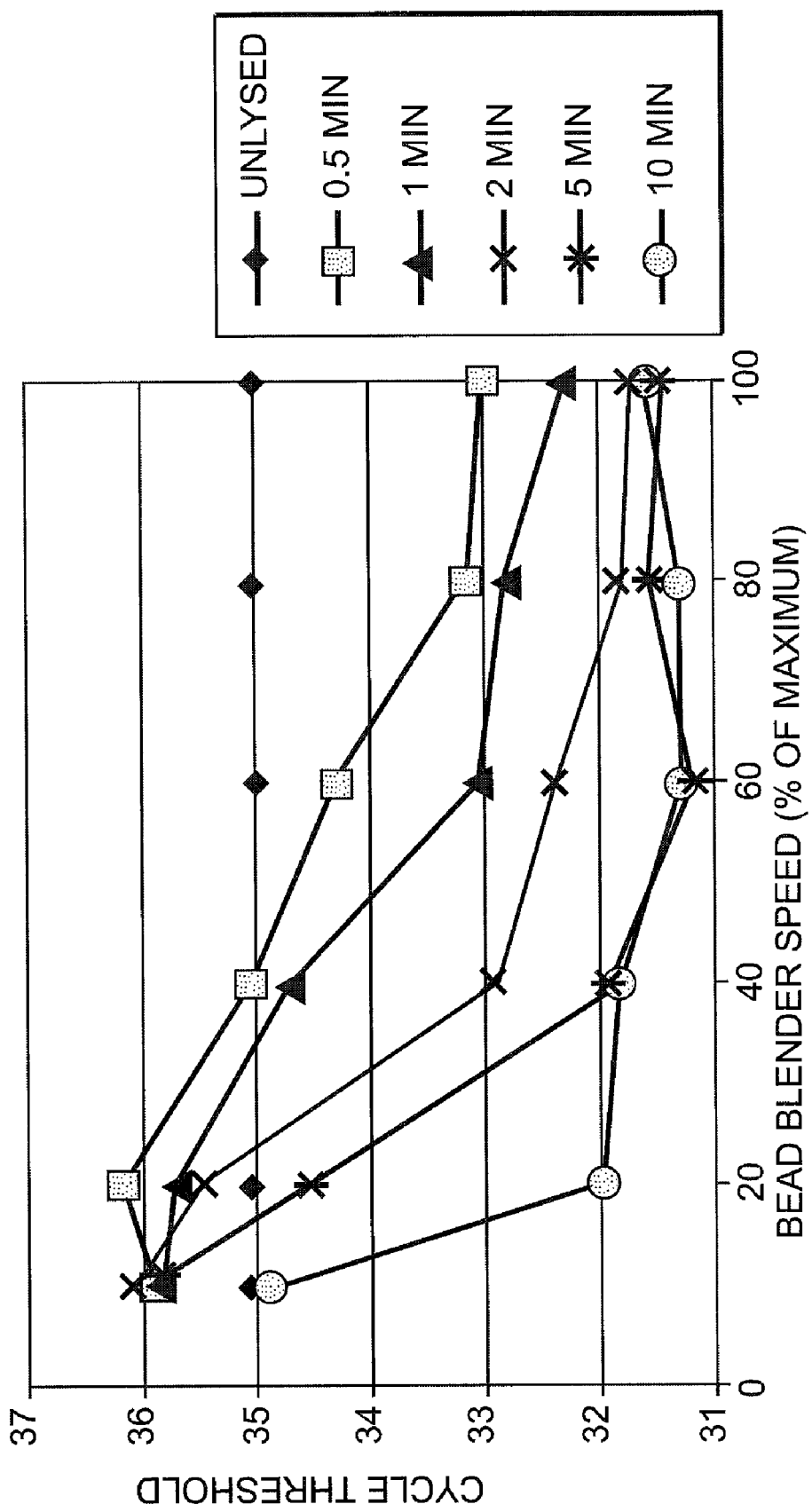

MAGNETIC LYSIS METHOD AND DEVICE

RELEVANT APPLICATIONS

This application claims the priority of U.S. Provisional Application No. 61/272,396, filed on Sep. 21, 2009, which is incorporated herein by reference in its entirety.

TECHNICAL FIELD

The technical field is biotechnology and, more specifically, methods and apparatus for lysing cells.

BACKGROUND

Cell lysis is the destruction, or disruption, of a cell's membrane or wall, which breaks open the cell and exposes its contents. Many techniques are available for the disruption of cells, including physical, chemical (e.g., detergent-based methods, chaotropic salts) and biochemical (e.g., enzymes such as lysozyme). Mechanical lysis, such as vortexing and bead-beating, is one form of physical lysis. Sonication is another form of physical lysis, which uses pulsed, high frequency sound waves to agitate and lyse cells, bacteria, spores, and finely diced tissue. These approaches, however, are not readily compatible with an integrated low-cost cell lysis/nucleic acid analysis system. Detergent-based methods are often easier to use with more efficient protocols than physical methods. Nonetheless, the presence of detergent may interfere with downstream reactions in an integrated system and can give variable lysis efficiencies for hardier bacteria and spores and require long incubation steps and or heat treatment. Therefore, there still exists a need for cell lysis methods that are cost-effective, efficient and compatible with an integrated cell lysis/analysis system.

SUMMARY

A method for lysing cells, virus particles and spores is disclosed. The method comprises stirring cells with a magnetic stir element in a container in the presence of a plurality of cell lysis beads, wherein the stir element rotates at a speed sufficient and duration to lyse the cells. In some embodiments, the cell lysis beads are selected from the group consisting of polymer beads, glass beads, ceramic beads and metal beads. In some embodiments, the cell lysis beads have diameters within the range of 10-1000 µm. In some embodiments, 1 mg-10 g of cell lysis beads are added to the lysis chamber. In some embodiments, 1 ul-10 ml of an aqueous liquid is added to the lysis chamber. In some embodiments, a sample or specimen is added directly to the lysis chamber alone. In some embodiments, a sample is added directly to the lysis chamber together with an aqueous liquid (e.g. a solid specimen that is homogenized and lysed to yield an aqueous form). In some embodiments, the magnetic stir element has a rectangular shape, a trapezoidal shape, a two-pronged tuning fork shape, a rod shape, and a bar shape. In some embodiments, the cells are eukaryotic cells, prokaryotic cells, endospores, or a combination thereof; and are suspended in a liquid medium at a concentration ranging from 1 to $1 \times 10^{10}$ cells/ml. In some embodiments, the cells are virus particles and are suspended in a liquid medium at a concentration ranging from 1 to $1 \times 10^{13}$ particles/ml.

Also disclosed is a method for lysing cells and virus particles. The method comprises suspending cells or virus particles in a liquid medium to form a suspension, and stirring the suspension with a magnetic stir element at high speed, between 1000-5000 rpm, preferably closer to 5000 rpm, in the presence of a plurality of cell lysis beads for a time period between 1-600 seconds, preferably about 90-120 seconds.

Also disclosed is a device for lysing cells and virus particles. The device includes a chamber having one or more magnetic stir elements and a plurality of cell lysis beads disposed therein. The chamber is dimensioned to allow rotation of the one or more magnetic stir elements inside the chamber. In some embodiments, the device further includes a magnetic stirrer that produces a rotating magnetic field, wherein the one or more magnetic stir elements rotate inside the chamber when placed within the operational range of the rotating magnetic field. In some embodiments, the device further includes a chamber holder configured to hold the chamber within the rotating magnetic field produced by the magnetic stirrer.

Also disclosed is a method for purifying nuclei acid from a cell. The method comprises applying a magnetic field to a vessel containing a cell, a stir element, and a plurality of beads, wherein the magnetic field causes the stir element to collide with the plurality of beads and produce a cell lysate; and isolating nuclei acid from the cell lysate.

Also disclosed is a method for amplifying a polynucleotide from a cell. The method comprises applying a magnetic field to a vessel containing a cell, a stir element, and a plurality of beads, wherein the magnetic field causes the stir element to collide with the plurality of beads and produce a cell lysate, and amplifying a polynucleotide from the cell lysate.

Also disclosed is a method for detecting a polynucleotide from a cell. The method comprises applying a magnetic field to a vessel containing a cell, a stir element, and a plurality of beads, wherein the magnetic field causes the stir element to collide with the plurality of beads and produce a cell lysate, and detecting a polynucleotide from the cell lysate. In certain embodiments, the detecting step comprises isolating nuclei acids from the cell lysate, amplifying the polynucleotide from isolated nuclei acids, and detecting the amplified polynucleotide.

BRIEF DESCRIPTION OF DRAWINGS

The detailed description will refer to the following drawings in which:

FIG. 10. is a graph showing the effect of lysis time and bead blender speed on the real-time PCR response for *Bacillus thuringiensis* spores. Efficient lysis of *Bacillus thuringiensis* spores was achieved in 2 minutes when the bead blender was operated at high-speed. Lower speeds required longer lysis times. Unlysed spores have low-levels of extracellular DNA that are detectable without lysis (0 min). A small amount of free DNA binds to the glass beads. Bead blender speed of 100 corresponds to 5000 rpm.

DETAILED DESCRIPTION

In describing preferred embodiments of the present invention, specific terminology is employed for the sake of clarity. However, the invention is not intended to be limited to the specific terminology so selected. It is to be understood that each specific element includes all technical equivalents which operate in a similar manner to accomplish a similar purpose.

Figure 1:
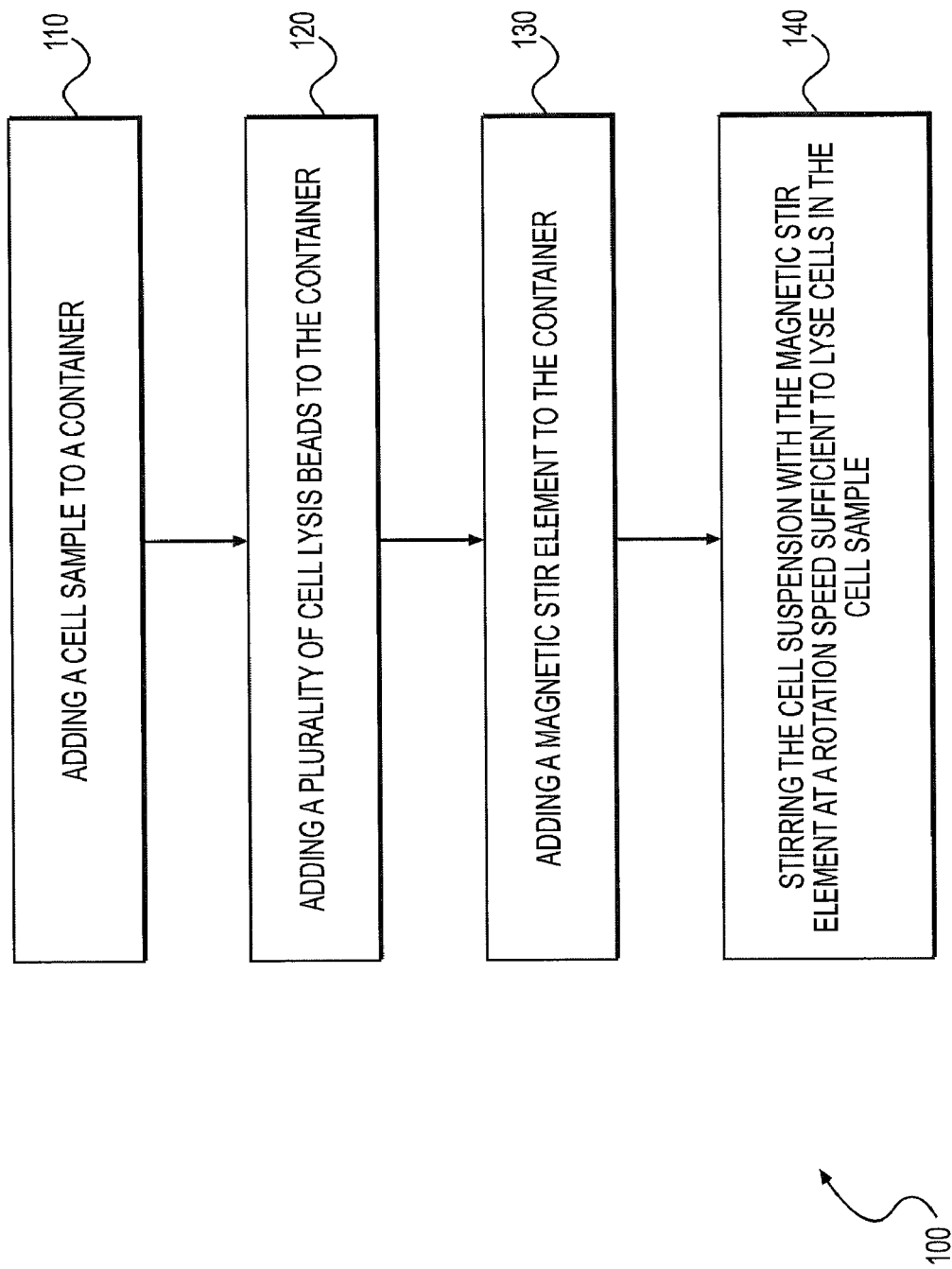
FIG. 1 is a flow chart showing an embodiment of a method for lysing cells.
Figure 2:
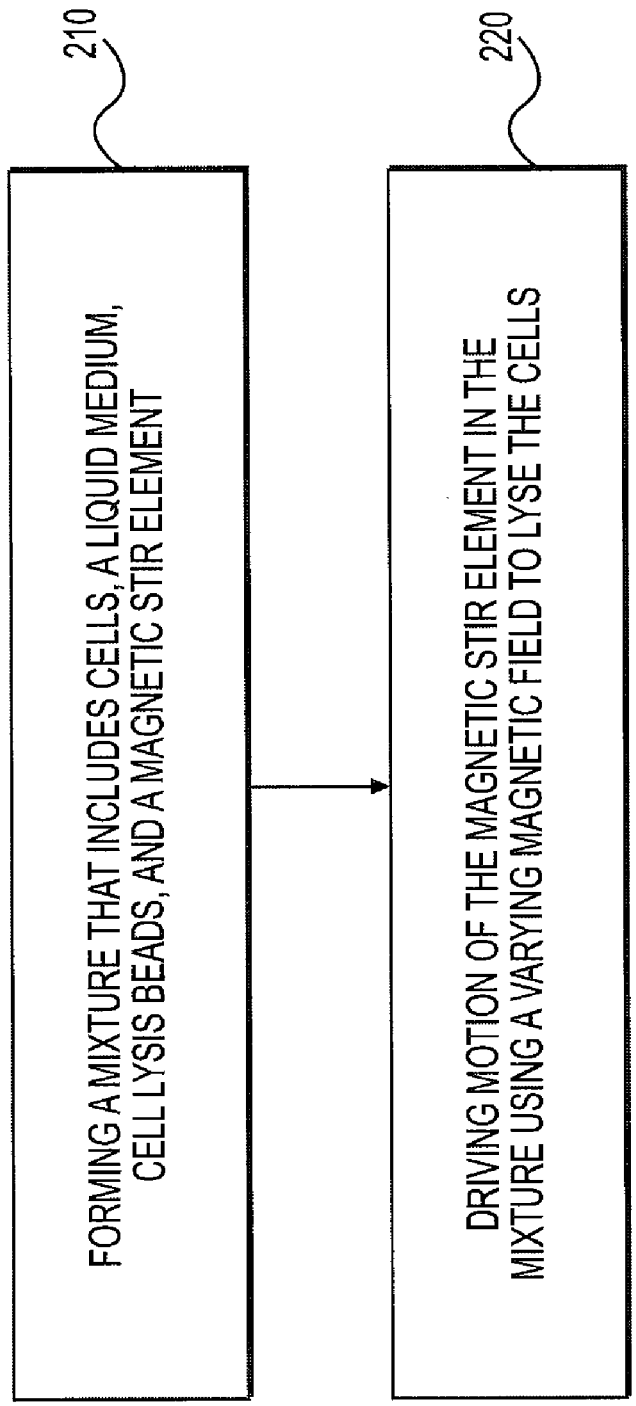
FIG. 2 is a flow chart showing another embodiment of a method for lysing cells.

Embodiments of a method for lysing cells are disclosed. Referring now to FIG. 1, in some embodiments, the method 100 includes adding a cell sample to a chamber (step 110), adding a plurality of cell lysis beads to the container (step 120), adding a magnetic stirring element to the container (step 130), and stirring the cell sample with the magnetic stir element at a rotation speed (between 1000 and 5000 rpm) sufficient to lyse the cells (step 140). Referring now to FIG. 2, in other embodiments, the method 200 includes forming a mixture that includes cells, a liquid medium, cell lysis beads, and a magnetic stir element (step 210), and driving motion of the magnetic stir element in the mixture using a varying magnetic field to lyse the cells (step 220).

As used herein, the term "cells" refers to eukaryotic cells, prokaryotic cells, viruses, endo-spores or any combination thereof. Cells thus may include bacteria, bacterial spores, fungi, virus particles, single-celled eukaryotic organisms (e.g., protozoans, yeast, etc.), isolated or aggregated cells from multi-cellular organisms (e.g., primary cells, cultured cells, tissues, whole organisms, etc.), or any combination thereof, among others.

The term "cell sample" refers to any cell-containing samples. As used herein, cell samples include specimens of human, plant, animal, food, agriculture or environmental origin, such nasal swab, blood, stool, plasma, tissue, leaves, water and soil samples. Preferably, the cell samples contain cells suspended in a liquid medium at a concentration that does not interfere with the movement of the magnetic stir element.

The term "lyse" with respect to cells means disruption of the integrity of at least a fraction of the cells to release intracellular components, such as nuclei acids and proteins, from the disrupted cells.

The term "homogenize" with respect to blending (diverse elements e.g. stool, tissue, sputum, saliva) into a uniform mixture.

Eukaryotic cells, prokaryotic cells, and/or viruses may be suspended at any suitable concentration. In some embodiments, eukaryotic cells and/or prokaryotic cells are suspended at a concentration ranging from 1 to $1 \times 10^{10}$ cells/ml, 1 to $1 \times 10^5$ cells/ml, or $1 \times 10^3$ to $1 \times 10^4$ cells/ml, among others. In some embodiments, virus particles are suspended in a concentration ranging from 1 to $1 \times 10^{13}$ particles/ml, 1 to $1 \times 10^{10}$ particles/ml, or $1 \times 10^5$ to $1 \times 10^7$ particles/ml.

The liquid medium can be isotonic, hypotonic, or hypertonic. In some embodiments, the liquid medium is aqueous. In certain embodiments, the liquid medium contains a buffer and/or at least one salt or a combination of salts. In some embodiments, the pH of the liquid medium ranges from about 5 to about 8, from about 6 to 8, or from about 6.5 to about 8.5. A variety of pH buffers may be used to achieve the desired pH. Suitable buffers include, but are not limited to, Tris, MES, Bis-Tris, ADA, ACES, PIPES, MOPSO, Bis-Tris propane, BES, MOPS, TES, HEPES, DIPSO, MOBS, TAPSO, HEPPSO, POPSO, TEA, HEPPS, Tricine, Gly-Gly, Bicine, and a phosphate buffer (e.g., sodium phosphate or sodium-potassium phosphate, among others). The liquid medium may comprise from about 10 mM to about 100 mM buffer, about 25 mM to about 75 mM buffer, or from about 40 mM to about 60 mM buffer, among others. The type and amount of the buffer used in the liquid medium can vary from application to application. In some embodiments, the liquid medium has a pH of about 7.4, which can be achieved using about 50 mM Tris buffer. In some embodiments the liquid medium in water.

The chamber can be a container of any suitable material, size, and shape. In certain embodiments, the chamber is a plastic container. The chamber may, for example, be in the shape of a micro centrifuge tube (e.g., an Eppendorf tube), a centrifuge tube, a vial, microwell plate. The chamber can define only one compartment/chamber for holding cells, beads, and a stir element, or a plurality of discrete compartments/chambers (e.g., an array of wells) for holding mixtures (cells, beads, and stir elements) in isolation from one another. The chamber may be a sealed or sealable container, such as a container with a lid, cap, or cover. The interior surface may be chemically inert to preserve the integrity of the analyte of interest.

The cell lysis beads can be any particle-like and/or bead-like structure that has a hardness greater than the hardness of the cells. The cell lysis beads may be made of plastic, glass, ceramic, metal and/or any other suitable materials. In certain embodiments, the cell lysis beads may be made of non-magnetic materials. In certain embodiments, the cell lysis beads are rotationally symmetric about at least one axis (e.g., spherical, rounded, oval, elliptic, egg-shaped, and droplet-shaped particles). In other embodiments, the cell lysis beads have polyhedron shapes. In some embodiments, the cell lysis beads are irregularly shaped particles. In some embodiments, the cell lysis beads are particles with protrusions. In certain embodiments, the amount of beads added to each lysis container is in the range of 1-10,000 mg, 1-1000 mg, 1-100 mg, 1-10 mg, among others.

In certain embodiments, the cell lysis beads have diameters in the range of 10-1,000 µm, 20-400 µm, or 50-200 µm, among others.

The magnetic stir element can be of any shape and should be small enough to be placed into the container and to move or spin or stir within the container. The magnetic stir element can be a bar-shaped, cylinder-shaped, cross-shaped, V-shaped, triangular, rectangular, rod or disc-shaped stir element, among others. In some embodiments, the magnetic stirring element has a rectangular shape. In some embodiments, the magnetic stirrer has a two-pronged tuning fork shape. In some embodiments, the magnetic stirrer has a V-like shape. In some embodiments, the magnetic stirrer has a trapezoidal shape. In certain embodiments, the longest dimension of the stir element is slightly smaller than the diameter of the container (e.g. about 75-95% of the diameter of the container). In certain embodiments, the magnetic stir element is coated with a chemically inert material, such as polymer, glass, or ceramic (e.g., porcelain). In certain embodiments, the polymer is a biocompatible polymer such as PTFE and paralyne.

The cell suspension, cell lysis beads and the magnetic stir element may be placed into the chamber in any order. In some embodiments, the cell suspension is added to the chamber before the cell lysis beads and the magnetic stirring element. In other embodiments, the cell lysis beads and/or the magnetic stirring element are placed into the chamber before the cells (e.g., before a cell suspension).

The chamber, and particularly the cells, beads, and magnetic stir element, are located within an operational range of a varying magnetic field. For example, the chamber may be located with an operational range of a rotating magnetic field (e.g., by placing the container on or adjacent to a magnetic stirrer). The varying magnetic field drives motion of the stir element, such as rotational motion, reciprocation, or a combination thereof, among others, which in turn drives motion of the beads, the cells, and the liquid medium. In some embodiments, the cell suspension is stirred with the magnetic stirring element at a rotation speed and for durations sufficient to lyse the cells inside the container. The appropriate rotation speed and duration are application dependent and can be empirically determined by a person of ordinary skill in the art. Generally speaking, the rotation speed sufficient to lyse the cells is determined by factors such as the type of cells, the concentration of cell suspension, the volume of the cell suspension, the size and shape of the magnetic stirring element, the amount/number, size, shape and hardness of the cell lysis beads, and the size and shape of the chamber.

In certain embodiments, the magnetic stirring element is rotating at a speed between 1000-6000 rpm, preferably about 5000 rpm, for a time period between 1-600 seconds, preferably about 90-120 seconds. In certain embodiments, a chamber (e.g., in the shape of a test tube or micro centrifuge tube) is placed in a rack on a magnetic stirrer (e.g., VP 710C1 Rotary Magnetic Tumble Stirrer, 5000 RPM, 14 cm Long Usable Stirring Deck, With Motor Housing And Plate Holder, Stirs 2 Deep Well Microplates Or 6 Standard Microplates— 115 Volts AC—60 Hz, V&P Scientific) and is stirred at the highest speed setting (>1000 rpm). In other embodiments, the chamber is a well in a microplate, such as an ELISA plate. In other embodiments, the chamber is a cylinder shaped chamber with a cell inlet and a cell outlet. In certain embodiments, the varying magnetic field is generated by rotating a magnet, preferably a permanent magnet, in the proximity of magnetic stir element. The magnet may be rotated above, below or by the side of the lysis chamber about an axis that passes through the center of the magnet. In certain embodiments, the chamber or chambers are placed at a position that is vertical to the surface the chamber or the chambers reside on and the magnet is rotated about an axis that is also vertical to the surface the chamber or the chambers reside on. In other embodiments, the chamber or chambers are placed at a position that is vertical to a the surface the chamber or the chambers reside on and the magnet is rotated about an axis that is parallel to the surface the chamber or the chambers reside on. In yet other embodiments, the chamber or chambers are placed at a position that is vertical to a the surface the chamber or the chambers reside on and the magnet is rotated about an axis that forms an angle with the surface the chamber or the chambers reside on. The angle is greater than 0 degree but smaller than 180 degrees. In other embodiments, the magnet also has an elongated shape and rotates about an axis that extends along the longest dimension of the magnet.

Figure 3:
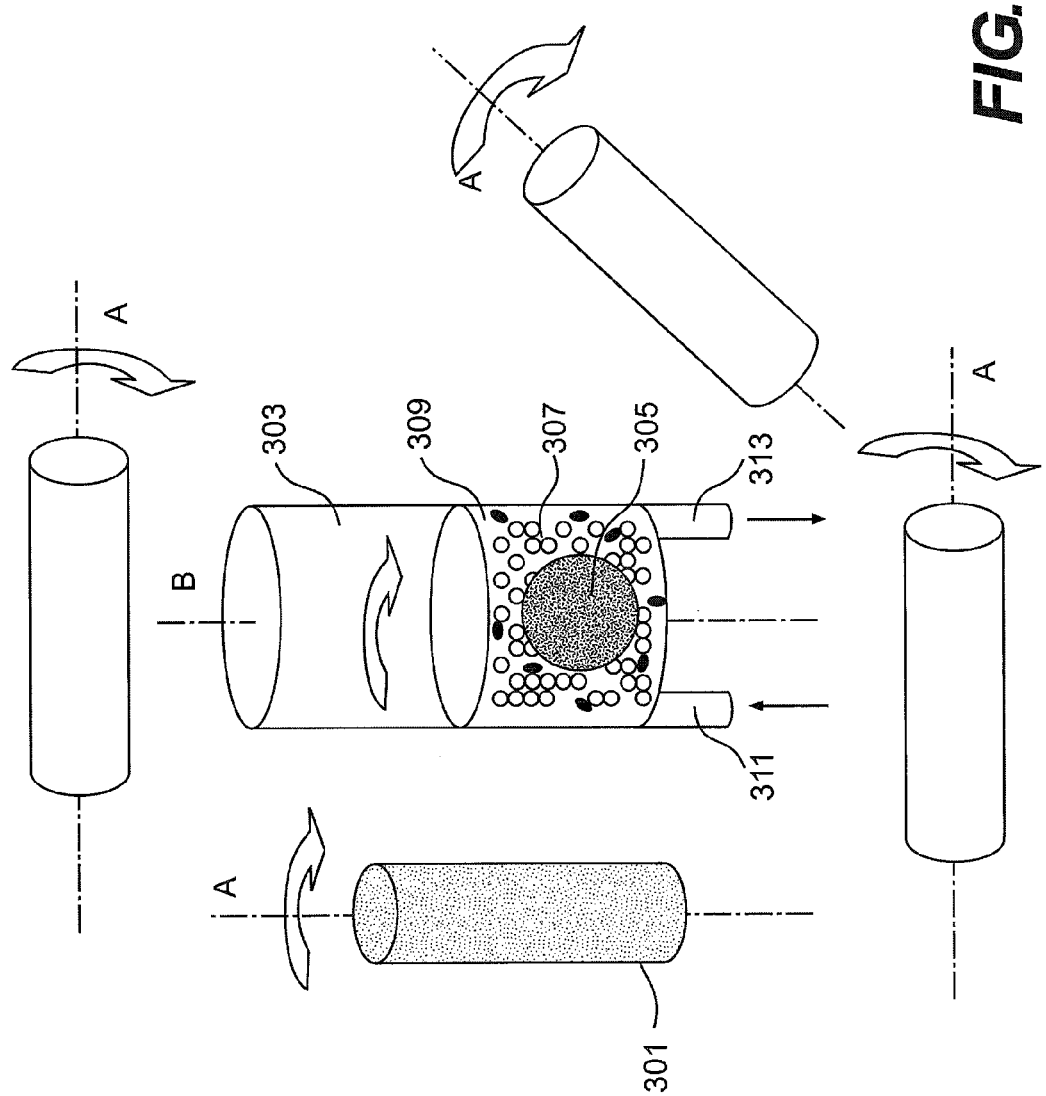
FIG. 3 is a graph showing relative positions of a magnet and a lysis chamber.

FIG. 3 shows the relative positions of a cylinder shaped magnet 301 and a lysis chamber 303. The magnet 301 rotates about an axis A and causes a magnet stir element 305 in the chamber 303 to rotate in the same direction along an axis B. The rotating magnet stir element 305 collides with beads 307 and lyse cells 309 in the process. The magnet 301 may be positioned alongside, above, below or diagonally from the chamber 303. In this embodiment, the chamber 303 has an inlet 311 and an outlet 313 to facilitate loading and unloading of the chamber.

In certain embodiments, the speed of rotation of the stirrer element is increased to increase lysis efficiency and reduces the time required to achieve lysis. In certain other embodiments, the speed of rotation is regulated so that only certain types of cells are lysed. For example, in a cell suspension containing multiple types of cells, the stir element may rotate at a first speed to lyse a first set of cells and then rotate at a second speed to lyse a second set of cells. In other embodiments, the container is coupled to a temperature regulation module that controls the temperature of the cell suspension before, during and/or after the lysing process. In certain embodiments, the temperature of the cell suspension is maintained at 8-2° C.

In certain embodiments, lysing of particular cell types can be facilitated by adding additives to the cell suspension prior to and/or during the stirring step. Examples of additives include enzymes, detergents, surfactants and other chemicals such as bases and acids. It has been found that alkaline conditions (e.g., 10 mM NaOH) may enhance the lysis efficiency during stirring for certain types of cells. The cell suspension may also or alternatively be heated during stirring to enhance the lysis efficiency. Additives, however, can be detrimental to downstream processing steps including nucleic acid amplification and detection. Eliminating the need for additives to achieve efficient lysis is desirable as specimen processing can be greatly simplified.

The stirrer/beads combination provides many advantages over conventional lysing methods. The stirrer/beads method is much faster than chemical and enzymatic approaches, and provides improved cell or virus lysis over many other types of physical lysis methods. The stirrer/beads method is also amenable to automation using robotics and/or microfluidics. The magnetic source is reusable and doesn't require precise alignment with the vessel, can drive a plurality of chambers. The magnetic stirrer element is low-cost to enable it to be single-use disposable.

Also disclosed is a device for lysing cells. The device includes a chamber having a magnetic stir element and a plurality of cell lysis beads disposed therein. A user may simply add a cell suspension into the chamber, place the chamber on a magnetic stirrer, and stir the cell suspension with the magnetic stir element at a speed sufficient to lyse the cells.

Also disclosed is a system for lysing cells. The system includes a chamber having a magnetic stir element and a plurality of cell lysis beads disposed therein, and a magnetic stirrer that produces a rotating magnetic field, wherein the magnetic stir element rotates inside the chamber when placed within an operational range of the rotating magnetic field.

In certain embodiments, the system further contains a rack configured to hold the chamber. The rack may be configured to hold multiple chambers and can be placed on a support surface of a magnetic stirrer for simultaneous processing of multiple samples. The rack may also be used as holder of the chamber for storage purpose. For example, multiple chambers may be placed on the rack and stored in a refrigerator or freezer for further analysis. The chamber may be interfaced with an external instrument (e.g. liquid handling robot, microfluidic device, analytical instrument).

Also disclosed is a method for purifying nuclei acid from a cell. The method comprises applying a magnetic field to a vessel containing a cell, a stir element, and a plurality of beads, wherein the magnetic field causes the stir element to collide with the plurality of beads and produce a cell lysate; and isolating nuclei acid from the cell lysate.

Also disclosed is a method for amplifying a polynucleotide from a cell. The method comprises applying a magnetic field to a vessel containing a cell, a stir element, and a plurality of beads, wherein the magnetic field causes the stir element to collide with the plurality of beads and produce a cell lysate, and amplifying a polynucleotide from the cell lysate.

Also disclosed is a method for detecting a polynucleotide from a cell. The method comprises applying a magnetic field to a vessel containing a cell, a stir element, and a plurality of beads, wherein the magnetic field causes the stir element to collide with the plurality of beads and produce a cell lysate, and detecting a polynucleotide from the cell lysate. In certain embodiments, the detecting step comprises isolating nuclei acids from the cell lysate, amplifying the polynucleotide from isolated nuclei acids, and detecting the amplified polynucleotide.

EXAMPLES

Example 1

Lysis of *E. coli* Cells

*E. coli* cells were suspended in Tris-EDTA buffer at a concentration of $10^4$ cells/ml One milliliter of the cell suspension was added to a chamber (2 ml plastic vial, Wheaton) containing 800 mg glass beads (106 µm or finer, Sigma G8893) and a magnetic stir disc (VP-7195 Super Tumble Stir Disc, V&P Scientific).

The plastic vial was then placed on a magnetic stirrer (VP 710C1 Rotary Magnetic Tumble Stirrer, 5000 RPM, V&P Scientific) and stirred at 5000 rpm for 30 seconds, 1 minute or 2 minutes. Positive control samples were processed using a bead beater (Mini Bead Beater-1, Biospec) according to the manufacturer's instructions for 2 minutes at 4800 rpm. Unprocessed cell suspensions were used as controls. The lysed cells and controls were then subjected to real-time PCR amplification of a specific gene using a Roche LightCycler 480. The amplification conditions were: 95° C. for 250 sec; then 45 cycles at 95° C. for 10 sec, 60° C. for 20 sec, and 72° C. for 10 sec; and 40° C. for 10 sec at the final cycle.

Figure 4:
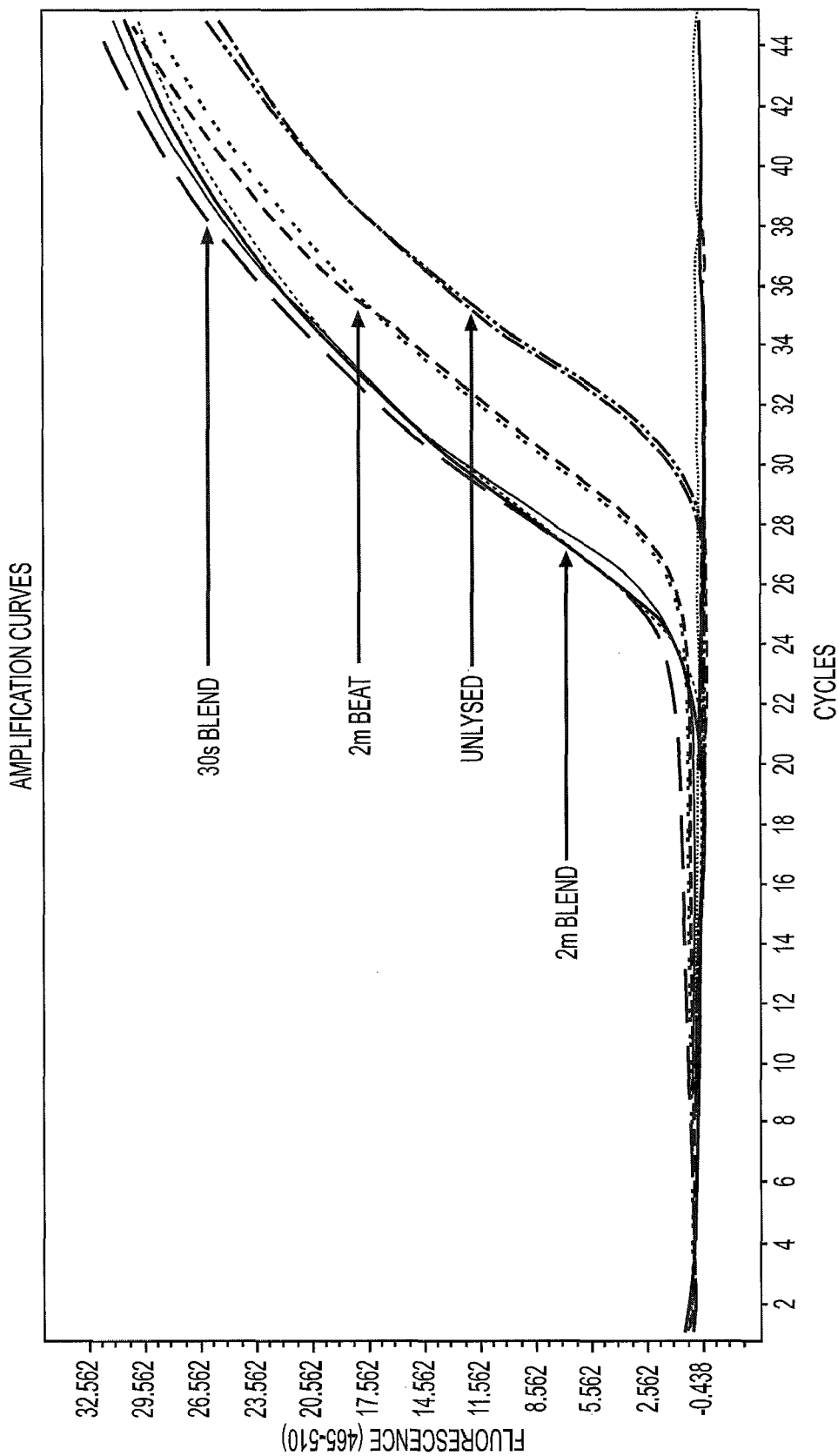
FIG. 4 is a graph showing real-time PCR amplification of a specific genomic region from unlysed *E. coli* cells (unlysed), *E. coli* cells lysed by bead beater for 2 minutes (2 m beat), and *E. coli* cells lysed by beads/stirrer for 30 seconds (30 s blend) or 2 minutes (2 m blend).
Figure 5:
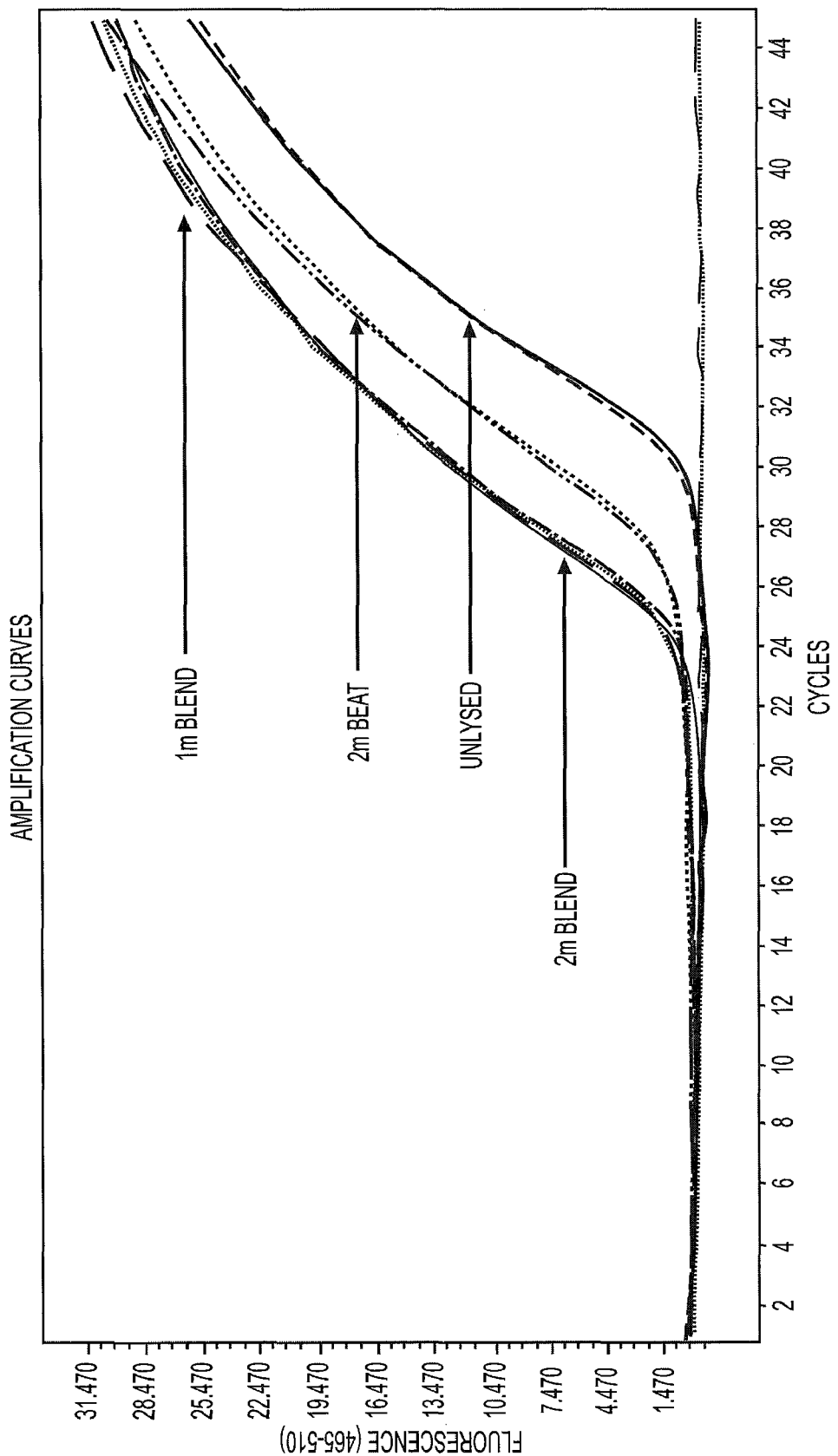
FIG. 5 is a graph showing real-time PCR amplification of a specific genomic region from unlysed *E. coli* cells (unlysed), *E. coli* cells lysed by a bead beater for 2 minutes (2 m beat), and *E. coli* cells lysed by beads/stirrer for 1 minute (1 m blend) or 2 minutes (2 m blend).
Figure 6:
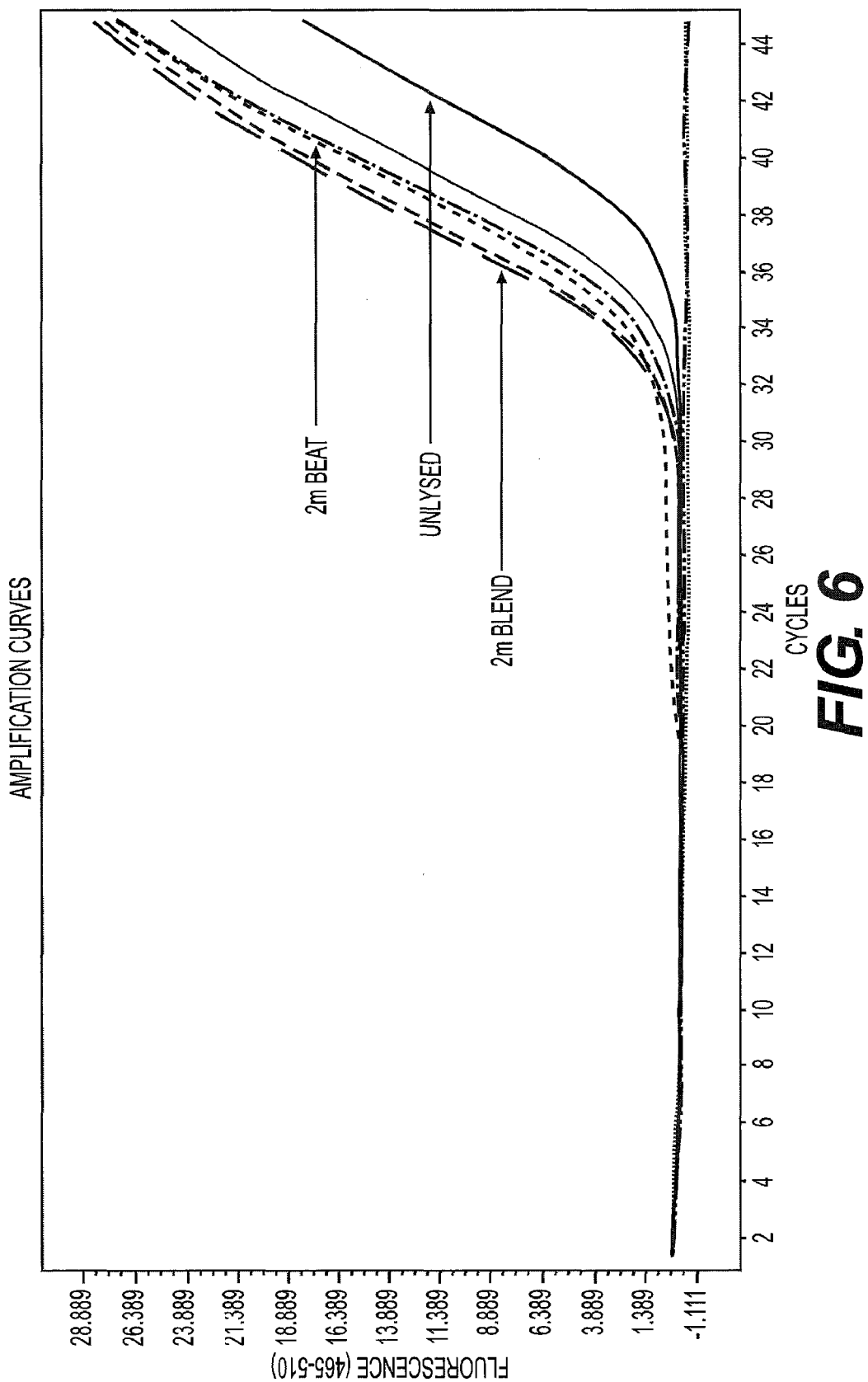
FIG. 6 is a graph showing real-time PCR amplification of a specific genomic region from unlysed *Bacillus thuringiensis* spores (unlysed), *Bacillus thuringiensis* spores lysed by a bead beater for 2 minutes (2 m beat), and *Bacillus thuringiensis* spores lysed by beads/stirrer for 2 minutes (2 m blend).
Figure 7:
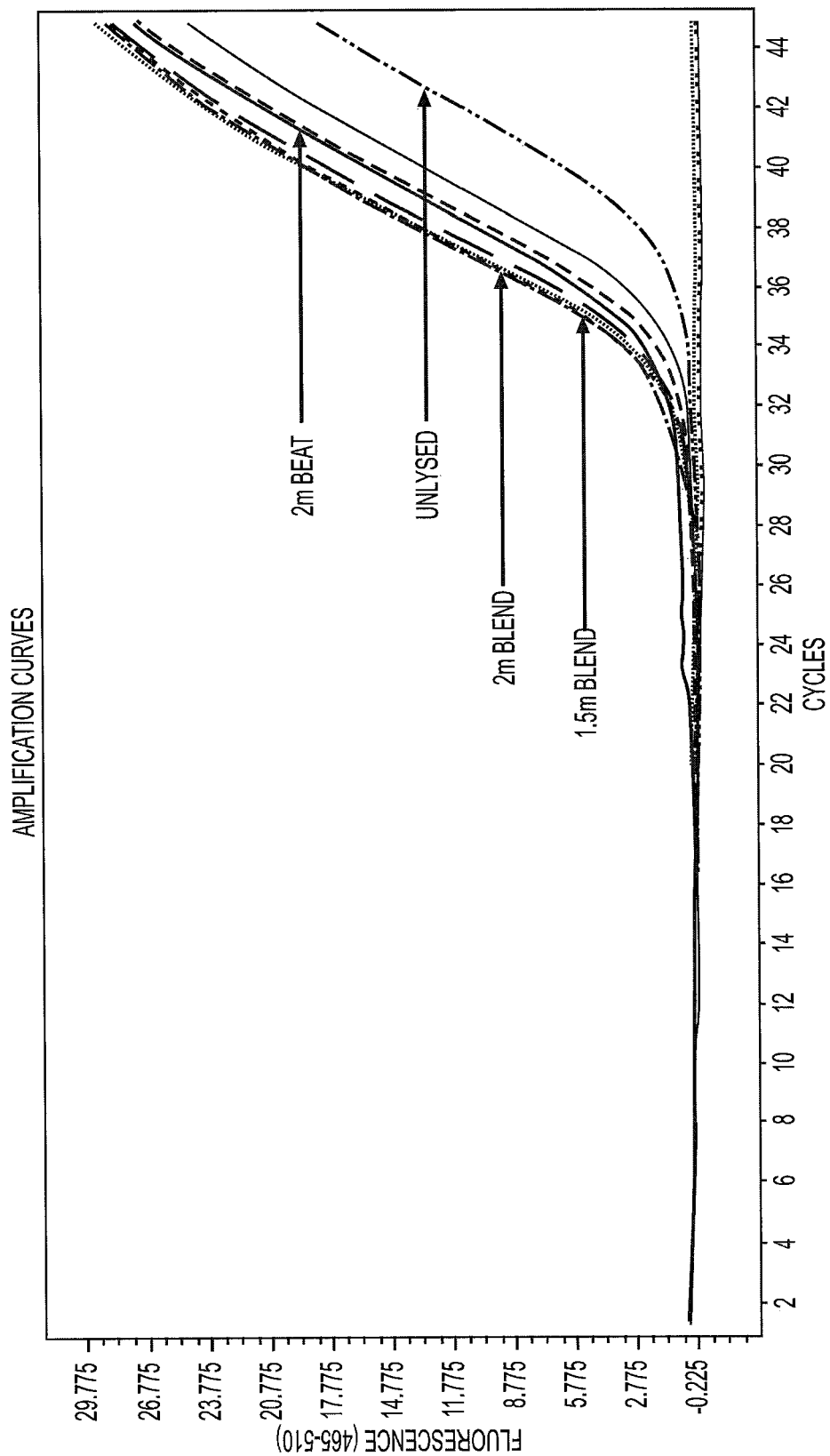
FIG. 7 is a graph showing real-time PCR amplification of a specific genomic region from unlysed *Bacillus thuringiensis* spores (unlysed), *Bacillus thuringiensis* spores lysed by bead beater for 2 minutes (2 m beat), and *Bacillus thuringiensis* spores lysed by beads/stirrer for 1.5 minutes (1.5 m blend) or 2 minutes (2 m blend).
Figure 8:
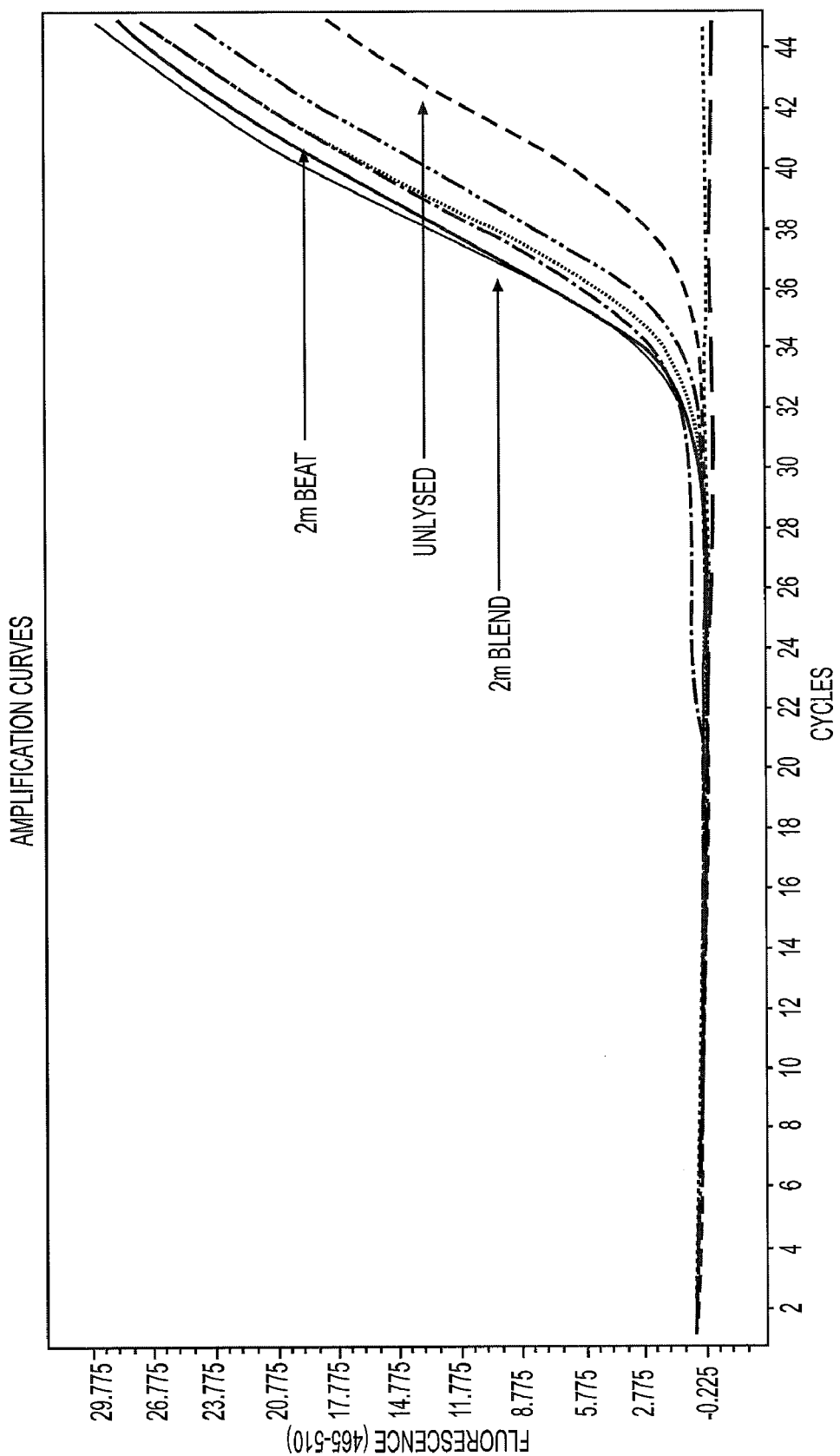
FIG. 8 is a graph showing real-time PCR amplification of a specific genomic region from unlysed *Bacillus thuringiensis* spores (unlysed), *Bacillus thuringiensis* spores lysed by bead beater for 2 minutes (2 m beat), and *Bacillus thuringiensis* spores lysed by beads/stirrer for 1.5 minutes (1.5 m blend).

As shown in FIGS. 4 and 5, the beads/stirrer method (30 s blend, 1 m blend and 2 m blend) provides better cell lysis than the bead beater method (2 m beat).

Example 2

Lysis of *Bacillus thuringiensis* Spores

*Bacillus thuringiensis* spores were suspended in water at a concentration of $10^4$ cells/ml. 500 µl of the cell suspension was added to a 2 ml plastic vial (Wheaton) containing 800 mg of glass beads (106 µm or finer, Sigma) and a magnetic stir disc (VP-7195 Super Tumble Stir Disc, V&P Scientific).

The plastic vial was then placed on a magnetic stirrer (VP 710C1 Rotary Magnetic Tumble Stirrer, 5000 RPM, V&P Scientific) and stirred at 5000 rpm for 1.5 minute or 2 minutes. Positive control samples were processed using a bead beater (Mini Bead Beater-1, Biospec) according to the manufacturer's instructions for 2 minutes. Unprocessed cell suspensions were used as controls. The lysed cells and controls were then subjected to real-time PCR amplification of a specific *B. thuringiensis* gene using a Roche LightCycler 480 under conditions described in Example 1.

As shown in FIGS. 3-6, the beads/stirrer method (1.5 m blend and 2 m blend) provides better cell lysis than the bead beater method (2 m beat).

Example 3

Effect of Lysis Time and Bead Blender Speed on the Real-Time PCR Response for *Staphylococcus aureus* Cells

*Staphylococcus aureus* cells were suspended and lysed at various blender speeds for various time periods using the same equipment and procedures described in Example 2.

Figure 9:
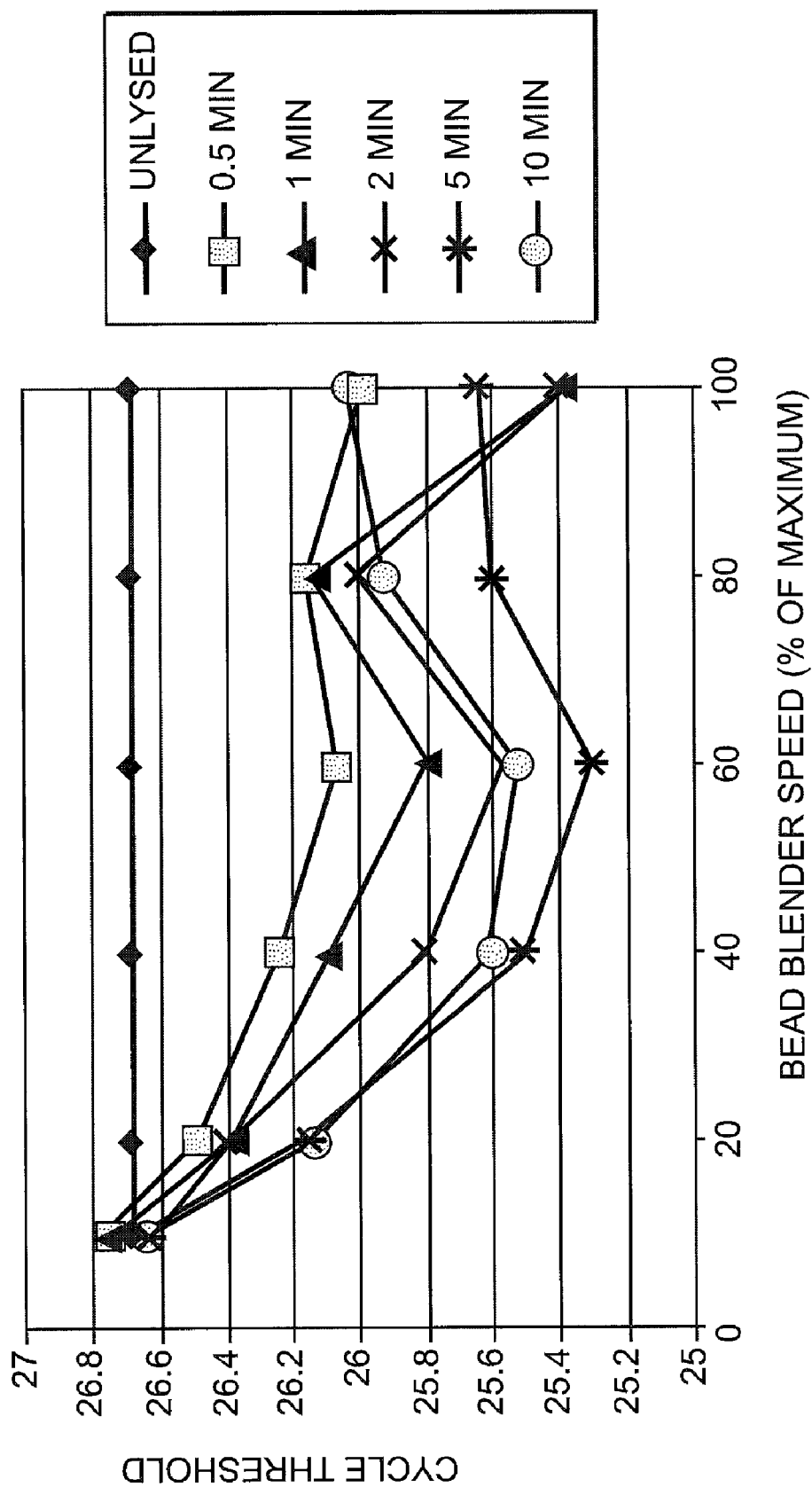
FIG. 9 is a graph showing the effect of lysis time and bead blender speed on the real-time PCR response for *Staphylococcus aureus* cells. Efficient lysis of *S. aureus* cells was achieved in 2 minutes when the bead blender was operated at high-speed. Lower speeds required longer lysis times. Unlysed spores have low-levels of extracellular DNA that are detectable without lysis (0 min). A small amount of free DNA binds to the glass beads. Bead blender speed of 100 corresponds to 5000 rpm.

FIG. 9 is a graph showing the effect of lysis time and bead blender speed on the real-time PCR response for *Staphylococcus aureus* cells. Efficient lysis of *S. aureus* cells was achieved in 2 minutes when the bead blender was operated at high-speed. Lower speeds required longer lysis times. Unlysed spores have low-levels of extracellular DNA that are detectable without lysis (0 min). A small amount of free DNA binds to the glass beads. Bead blender speed of 100 corresponds to 5000 rpm.

Example 4

Effect of Lysis Time and Bead Blender Speed on the Real-Time PCR Response for *Bacillus thuringiensis* Spores

*Bacillus thuringiensis* spores were suspended and lysed at various blender speeds for various time periods using the same equipment and procedures described in Example 2.

FIG. 10. is a graph showing the effect of lysis time and bead blender speed on the real-time PCR response for *Bacillus thuringiensis* spores. Efficient lysis of *Bacillus thuringiensis* spores was achieved in 2 minutes when the bead blender was operated at high-speed. Lower speeds required longer lysis times. Unlysed spores have low-levels of extracellular DNA that are detectable without lysis (0 min). A small amount of free DNA binds to the glass beads. Bead blender speed of 100 corresponds to 5000 rpm.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A method for lysing cells, comprising:
   stirring a liquid suspension containing one or more cells of interest with a magnetic stir element in a chamber in the presence of a plurality of beads, wherein said magnetic stir element drives motion of said plurality of beads and collides with said beads and wherein said magnetic stir element rotates at a speed for a period of time sufficient to lyse said one or more cells of interest.

2. The method of claim 1, further comprising: suspending said one or more cells in a liquid medium and forming said liquid suspension.

3. The method of claim 1, wherein said beads comprises a material selected from the group consisting of plastics, glass, ceramics, and metals.

4. The method of claim 3, wherein said beads are silica beads.

5. The method of claim 1, wherein said beads have diameters within the range of 10-1000 µm.

6. The method of claim 1, wherein said magnetic stir element comprises a metal or an alloy.

7. The method of claim 1, wherein said magnetic stir element has a shape selected from the group consisting of circular shape, square shape, rectangular shape, curved rod shape, cross-section rectangular shape, disc shape, rod shape, annulus shape, crescent shape, trapezoidal shape and two-pronged tuning fork shape.

8. The method of claim 1, wherein said cells of interest are eukaryotic cells or prokaryotic cells and wherein said liquid suspension contains said cells at a concentration ranging from 1 to $1\times10^{10}$ cells/ml.

9. The method of claim 1, wherein said magnetic stir element rotates at a speed of 1000-6000 rpm and said period of time is 90-120 seconds.

10. A method for lysing a cell, comprising:
    applying a magnetic field to a chamber comprising a cell of interest, a stirrer element, and a plurality of beads, wherein said magnetic field causes said stirrer element to rotate at a speed for a period of time so that said stirrer element collides with said beads with enough force to cause disintegration of said cell.

11. The method of claim 10, wherein said beads comprise glass beads, plastic beads, ceramic beads, metal beads or a mixture thereof.

12. The method of claim 10, wherein said stirrer element comprises stainless steel.

13. The method of claim 10, wherein said stirrer element comprises an alloy core coated with a polymer.

14. The method of claim 13, wherein said alloy core comprises neodymium iron boron or samarium cobalt.

15. The method of claim 13, wherein said polymer is a biocompatible polymer.

16. The method of claim 15, wherein said biocompatible polymer is polytetrafluoroethylene (PTFE) or parylene.

17. A method for purifying nucleic acids from a cell, comprising:
    applying a magnetic field to a vessel containing said cell, a stir element, and a plurality of beads, wherein said magnetic field causes said stir element to rotate at a speed for a period of time so that said stir element collides with said plurality of beads, thereby producing a cell lysate; and
    isolating nucleic acids from said cell lysate.

18. The method of claim 17, wherein said magnetic stir element rotates at a speed of 1000-6000 rpm and said period of time is 30 or 120 seconds.

19. A method for amplifying a polynucleotide from a cell, comprising:
    applying a magnetic field to a vessel containing said cell, a stir element, and a plurality of beads, wherein said magnetic field causes said stir element to rotate at a speed for a period of time so that said stir element collides with said plurality of beads, thereby producing a cell lysate; and
    amplifying said polynucleotide from said cell lysate.

20. The method of claim 19, wherein said magnetic stir element rotates at a speed of 1000-6000 rpm and said period of time is 30 or 120 seconds.

21. A method for detecting a polynucleotide from a cell, comprising:
    applying a magnetic field to a vessel containing said cell, a stir element, and a plurality of beads, wherein said magnetic field causes said stir element to rotate at a speed for a period of time so that said stir element collides with said plurality of beads, thereby producing a cell lysate; and
    detecting said polynucleotide from said cell lysate.

22. The method of claim 21, wherein said detecting step comprises:
    isolating nucleic acids from said cell lysate and producing isolated nucleic acids;
    amplifying said polynucleotide from said isolated nucleic acids and producing amplified polynucleotides; and
    detecting said amplified polynucleotides.

23. The method of claim 21, wherein said magnetic stir element rotates at a speed of 1000-6000 rpm and said period of time is 30 or 120 seconds.

* * * * *

UNITED STATES PATENT AND TRADEMARK OFFICE
CERTIFICATE OF CORRECTION

PATENT NO. : 8,399,190 B2  
APPLICATION NO. : 12/886144  
DATED : March 19, 2013  
INVENTOR(S) : Phillip Belgrader et al.

Page 1 of 1

It is certified that error appears in the above-identified patent and that said Letters Patent is hereby corrected as shown below:

In the Specification

Column 2, line 17: Please change "nuclei" to --nucleic--
          line 22: Please change "nuclei" to --nucleic--
          line 35: Please change "nuclei" to --nucleic--
          line 37: Please change "nuclei" to --nucliec--
Column 4, line 3: Please change "nuclei" to --nucleic--
          line 36: Please change "in" to --is--
Column 6, line 3: Please change "to a the surface" to --to [[a]] the surface--
          line 6: Please change "to a the surface" to --to [[a]] the surface--
Column 7, line 23: Please change "nuclei" to --nucleic--
          line 26: Please change "nuclei" to --nucleic--
          line 38: Please change "nuclei" to --nucleic--

Signed and Sealed this  
Seventeenth Day of September, 2013

Teresa Stanek Rea  
*Deputy Director of the United States Patent and Trademark Office*

UNITED STATES PATENT AND TRADEMARK OFFICE
CERTIFICATE OF CORRECTION

PATENT NO. : 8,399,190 B2
APPLICATION NO. : 12/886144
DATED : March 19, 2013
INVENTOR(S) : Phillip Belgrader et al.

It is certified that error appears in the above-identified patent and that said Letters Patent is hereby corrected as shown below:

Title Page, Item (73) Assignees: Please change "Quantilife, Inc." to --Quantalife, Inc.--

Signed and Sealed this
Twenty-eighth Day of January, 2014

Michelle K. Lee
*Deputy Director of the United States Patent and Trademark Office*